United States Patent [19]

Kondo et al.

[11] 4,016,186
[45] Apr. 5, 1977

[54] β-PHENOXY OR SUBSTITUTED PHENOXY ETHANOL COMPOUNDS

[75] Inventors: Kiyosi Kondo, Yamato; Osamu Terada; Kohei Oshima, both of Machida; Yasuki Mori, Kawasaki; Kenichi Mochida, Hiratsuka, all of Japan

[73] Assignees: Kyowa Hakko Kogyo Co., Ltd.; Sagami Chemical Research Center, both of Tokyo, Japan; part interest to each

[22] Filed: Nov. 26, 1974

[21] Appl. No.: 527,417

[52] U.S. Cl. ..................... 260/473 R; 260/468 R; 260/488 CD; 260/592; 260/611 A; 424/308
[51] Int. Cl.² ......................................... C07C 69/76
[58] Field of Search .................... 260/473 R, 473 S

[56] References Cited
UNITED STATES PATENTS

| | | | |
|---|---|---|---|
| 2,471,023 | 5/1949 | Cook et al. | 260/473 R |
| 2,806,054 | 9/1957 | Eden | 260/590 |
| 3,734,947 | 5/1973 | Ueno et al. | 260/473 R |
| 3,868,406 | 2/1975 | Siddall | 260/473 R |

FOREIGN PATENTS OR APPLICATIONS

| | | |
|---|---|---|
| 1,950,093 | 4/1970 | Germany |
| 6,920,474 | 9/1969 | Japan |

*Primary Examiner*—Paul J. Killos
*Attorney, Agent, or Firm*—Fitzpatrick, Cella, Harper & Scinto

[57] ABSTRACT

Novel β-phenoxy- or substituted phenoxy-ethanol compounds or esters thereof expressed by the formula

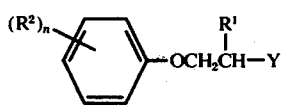

wherein $R^1$ is a hydrogen atom or an alkyl group, $R^2$ is a hydrogen atom or a substituent, Y is —OH group or group

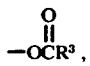

$R^3$ is an alkyl group, and $n$ is an integer of 1 to 3.

These compounds have juvenile hormone activities, and are useful for hormonal pest control and increased production of silkworm cocoons.

8 Claims, No Drawings

β-PHENOXY OR SUBSTITUTED PHENOXY ETHANOL COMPOUNDS

This invention relates to novel β-phenoxy or substituted phenoxy ethanol compounds. More specifically, this invention relates to compounds having juvenile homone activities an insects.

Juvenile hormone is known as an active substance which acts on the metamorphosis of insect larvae, and three compounds have been known so far to belong to this category as natural products. [B. M. Trost, Account Chem. Res., 3, 120(1970)]. These compounds, however, are unstable and cannot be utilized commercially.

We have now found stable novel compounds having a high juvenile hormone activity, which are β-phenoxy- or substituted phenoxy-ethanols, or esters of these, expressed by the following formula

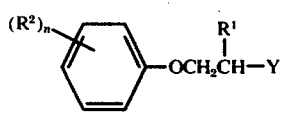

(I)

wherein $R^1$ is a hydrogen atom or an alkyl group, preferably a straight-chain, branched-chain or cyclic alkyl group containing 1 to 6 carbon atoms; $R_2$ is a hydrogen atom or a substituent, preferably an alkyl, alkoxy or carboalkoxy group containing 1 to 6 carbon atoms in the alkyl moiety, an acyl group, a halogen atom, a nitro group or a nitrile group; Y is –OH group or

group; $R^3$ is an alkyl group, preferably a straight-chain, branched-chain or cyclic alkyl group containing 1 to 12 carbon atoms; and $n$ is an integer of 1 to 3, preferably 1.

Typical examples of the compounds of this invention are given in the following Tables 1 and 2.

Table 1

| Compound No. | $R^2$ | $R^1$ | $R^3$ |
|---|---|---|---|
| 1 | p-$CO_2C_2H_5$ | $C_2H_5$ | t-$C_4H_9$ |
| 2 | " | " | i-$C_4H_9$ |
| 3 | " | " | i-$C_3H_7$ |
| 4 | " | $CH_3$ | t-$C_4H_9$ |
| 5 | " | " | i-$C_4H_9$ |
| 6 | " | " | i-$C_3H_7$ |
| 7 | p-$COCH_3$ | $C_2H_5$ | t-$C_4H_9$ |
| 8 | " | " | i-$C_4H_9$ |
| 9 | " | " | i-$C_3H_7$ |
| 10 | p-$COCH_3$ | $CH_3$ | t-$C_4H_9$ |

Table 1-continued

| Compound No. | $R^2$ | $R^1$ | $R^3$ |
|---|---|---|---|
| 11 | " | " | i-$C_4H_9$ |
| 12 | " | " | i-$C_3H_7$ |
| 13 | p-$C_2H_5$ | $C_2H_5$ | t-$C_4H_9$ |
| 14 | " | " | i-$C_4H_9$ |
| 15 | " | " | i-$C_3H_7$ |
| 16 | " | $CH_3$ | t-$C_4H_9$ |
| 17 | " | " | i-$C_4H_9$ |
| 18 | " | " | i-$C_3H_7$ |
| 19 | p-Cl | $C_2H_5$ | t-$C_4H_9$ |
| 20 | " | " | i-$C_4H_9$ |
| 21 | " | " | i-$C_3H_7$ |
| 22 | " | $CH_3$ | t-$C_4H_9$ |
| 23 | " | " | i-$C_4H_9$ |
| 24 | " | " | i-$C_3H_7$ |
| 25 | p-$CO_2CH_3$ | $C_2H_5$ | t-$C_4H_9$ |
| 26 | " | " | i-$C_3H_7$ |
| 27 | p-$CO_2C_3H_7$ | " | t-$C_4H_9$ |
| 28 | " | " | i-$C_3H_7$ |
| 29 | p-$OCH_3$ | $C_2H_5$ | t-$C_4H_9$ |
| 30 | " | " | i-$C_3H_7$ |
| 31 | p-$CO_2C_2H_5$ | " | $CH_3$ |
| 32 | " | " | n-$C_{11}H_{23}$ |
| 33 | p-$CO_2H$ | " | t-$C_4H_9$ |
| 34 | " | " | i-$C_3H_7$ |
| 35 | m-$CO_2CH_3$ | " | t-$C_4H_9$ |
| 36 | " | " | i-$C_3H_7$ |
| 37 | m-$CH_3$ | $CH_3$ | $CH_3$ |
| 38 | m-$CO_2CH_3$ | " | t-$C_4H_9$ |
| 39 | " | " | i-$C_3H_7$ |
| 40 | m-$OCH_3$ | $C_2H_5$ | t-$C_4H_9$ |
| 41 | " | " | i-$C_3H_7$ |
| 42 | m-$C_2H_5$ | " | t-$C_4H_9$ |
| 43 | " | " | i-$C_3H_7$ |
| 44 | o-$OCH_3$ | " | t-$C_4H_9$ |
| 45 | " | " | i-$C_3H_7$ |
| 46 | o-$C_2H_5$ | " | t-$C_4H_9$ |
| 47 | " | " | i-$C_3H_7$ |

Table 2

| Compound No. | $R^2$ | $R^1$ |
|---|---|---|
| 48 | p-$CO_2C_2H_5$ | $C_2H_5$ |
| 49 | " | $CH_3$ |
| 50 | p-$COCH_3$ | $C_2H_5$ |
| 51 | " | $CH_3$ |
| 52 | p-$C_2H_5$ | $C_2H_5$ |
| 53 | " | $CH_3$ |
| 54 | p-Cl | $C_2H_5$ |
| 55 | " | $CH_3$ |
| 56 | p-$OCH_3$ | $C_2H_5$ |
| 57 | p-$CO_2H$ | " |
| 58 | m-$CO_2CH_3$ | " |
| 59 | m-$CH_3$ | $CH_3$ |
| 60 | o-$OCH_3$ | $C_2H_5$ |

The nuclear magnetic resonance spectra of the compounds of Tables 1 and 2 are shown in Table 3 below.

In Table 3, $s$ stands for singlet; $d$, doublet; $t$, triplet; $q$, quartet; $m$, multiplet.

Table 3

| Compound No. | ($\delta$) ppm from TMs in $CDCl_3$ | | |
|---|---|---|---|
| 1 | 8.00(2H-d) | 6.93(2H-d) | 5.10(1H-m) |
|   | 4.33(2H-q) | 4.05(2H-d) | 1.75(2H-m) |
|   | 1.33(3H-t) | 1.16(9H-s) | 0.95(3H-t) |

Table 3-continued

| Compound No. | (δ) ppm from TMs in CDCl₃ | | | |
|---|---|---|---|---|
| 2 | 8.65(2H-d)<br>4.33(2H-q)<br>1.63(2H-m) | 6.96(2H-d)<br>4.13(2H-d)<br>0.91–1.5(14H-m) | 5.23(1H-m)<br>2.20(3H-m) | |
| 3 | 8.03(2H-d)<br>4.10(2H-d)<br>1.20(6H-d) | 6.95(2H-d)<br>2.51(1H-m)<br>1.00(3H-5) | 5.20(1H-m)<br>1.70(2H-m) | 4.35(2H-q)<br>1.34(3H-t) |
| 4 | 8.10(2H-d)<br>4.33(2H-q)<br>1.3–1.5(6H-m) | 7.00(2H-d)<br>4.11(2H-d) | 5.30(1H-m)<br>1.26(9H-s) | |
| 5 | 8.03(2H-d)<br>4.33(2H-q)<br>0.9–1.6(14H-m) | 6.96(2H-d)<br>4.05(2H-d) | 5.31(1H-m)<br>2.18(3H-m) | |
| 6 | 8.06(2H-d)<br>4.32(2H-q)<br>1.1–1.5(12H-m) | 6.96(2H-d)<br>4.06(2H-d) | 5.31(1H-m)<br>2.60(1H-m) | |
| 7 | 7.95(2H-d)<br>4.07(2H-d)<br>1.18(9H-s) | 6.95(2H-d)<br>2.50(3H-s)<br>0.93(3H-t) | 5.17(1H-m)<br>1.65(2H-d) | |
| 9 | 7.96(2H-d)<br>4.13(2H-d)<br>1.73(2H-m) | 6.95(2H-d)<br>2.50(3H-s)<br>1.18(6H-d) | 5.20(1H-m)<br>∼25(1H-m)<br>0.98(3H-t) | |
| 10 | 7.93(2H-d)<br>4.07(2H-d)<br>1.18(9H-s) | 6.93(2H-d)<br>2.51(3H-s) | 5.26(1H-m)<br>1.30(3H-d) | |
| 11 | 7.93(2H-d)<br>4.08(2H-d)<br>1.31(3H-d) | 6.93(2H-d)<br>2.50(3H-s)<br>∼1.0(6H-d) | 5.30(1H-m)<br>2.18(3H-m) | |
| 12 | 7.95(2H-d)<br>4.01(2H-d)<br>1.28(3H-d) | 6.95(2H-d)<br>2.50(3H-s)<br>1.13(6H-d) | 5.28(1H-m)<br>∼2.5(1H-m) | |
| 13 | 7.16(2H-d)<br>4.01(2H-d)<br>1.19(9H-s) | 6.84(2H-d)<br>2.55(2H-q)<br>1.17(3H-t) | 5.17(1H-m)<br>1.74(2H-m)<br>0.97(3H-t) | |
| 14 | 7.18(2H-d)<br>4.03(2H-d)<br>1.69(2H-m) | 6.90(2H-d)<br>2.56(2H-q)<br>0.9–1.3(12H-m) | 5.21(1H-m)<br>∼2.2(3H-m) | |
| 15 | 7.22(2H-d)<br>4.03(2H-d)<br>0.9–1.3(12H-m) | 6.92(2H-d)<br>∼2.52(3H-m) | 5.18(1H-m)<br>1.67(2H-m) | |
| 16 | 7.20(2H-d)<br>4.02(2H-d)<br>1.20(9H-s) | 6.92(2H-d)<br>2.57(2H-q) | 5.28(1H-m)<br>1.30(3H-d) | |
| 17 | 7.18(2H-d)<br>3.98(2H-d)<br>0.8–1.4(12H-m) | 6.85(2H-d)<br>2.57(2H-q) | 5.29(1H-m)<br>∼2.1(3H-m) | |
| 18 | 7.15(2H-d)<br>4.00(2H-d)<br>1.0–1.4(12H-m) | 6.84(2H-d)<br>2.57(2H-q) | 5.27(1H-m)<br>∼2.5(1H-m) | |
| 22 | 7.25(2H-d)<br>3.98(2H-d) | 6.88(2H-d)<br>1.28(3H-d) | 5.28(1H-m)<br>1.18(9H-s) | |
| 23 | 7.27(2H-d)<br>3.97(2H-d)<br>1.30(3H-d) | 6.92(2H-d)<br>2.18(2H-d)<br>∼1.3(6H-m) | 5.30(1H-m)<br>∼2.2(1H-m) | |
| 24 | 7.27(2H-d)<br>3.98(2H-d)<br>1.14(6H-d) | 6.88(2H-d)<br>2.50(2H-m) | 5.26(1H-m)<br>1.29(3H-d) | |
| 25 | 7.98(2H-d)<br>4.08(2H-d)<br>1.18(9H-s) | 6.92(2H-d)<br>3.90(3H-s)<br>0.97(3H-t) | 5.14(1H-m)<br>∼1.7(2H-m) | |
| 26 | 8.00(2H-d)<br>4.09(2H-d)<br>1.70(2H-m) | 6.93(2H-d)<br>3.90(3H-s)<br>1.18(6H-d) | 5.18(1H-m)<br>2.53(1H-m)<br>0.99(3H-t) | |
| 27 | 8.03(2H-d)<br>4.08(2H-d)<br>1.18(9H-s) | 6.95(2H-d)<br>4.19(2H-q)<br>∼1.1(6H-m) | 5.18(1H-m)<br>1.67(4H-m) | |
| 28 | 7.96(2H-d)<br>4.19(2H-q)<br>∼1.3(4H-m) | 6.84(2H-d)<br>4.04(2H-d)<br>0.9–1.2(12H-m) | 5.14(1H-m)<br>2.52(1H-m) | |
| 29 | 6.75(4H-s)<br>3.68(3H-s)<br>0.95(3H-t) | 5.10(1H-m)<br>1.67(2H-m) | 3.97(2H-d)<br>1.18(9H-s) | |
| 30 | 6.71(4H-s)<br>3.62(3H-s)<br>1.14(6H-d) | 5.10(1H-m)<br>2.80(1H-m)<br>0.96(3H-t) | 3.93(2H-d)<br>1.65(2H-m) | |
| 31 | 8.03(2H-d)<br>4.33(2H-q)<br>1.70(2H-m) | 6.98(2H-d)<br>4.09(2H-d)<br>1.34(3H-t) | 5.18(1H-m)<br>2.07(3H-s)<br>0.96(3H-t) | |
| 32 | 8.05(2H-d)<br>4.33(2H-q)<br>0.9–1.9(30H-m) | 6.94(2H-d)<br>4.07(2H-d) | 5.19(1H-m)<br>2.28(2H-m) | |
| 33 | 8.01(2H-d)<br>4.09(2H-d)<br>0.99(3H-t) | 6.92(2H-d)<br>1.67(2H-m) | 5.17(1H-m)<br>1.18(9H-s) | |
| 34 | 8.03(2H-d)<br>4.14(2H-d)<br>1.18(6H-d) | 6.95(2H-d)<br>2.80(1H-m)<br>1.00(3H-t) | 5.22(1H-m)<br>1.62(2H-m) | |
| 35 | 7.0–7.7(4H-m)<br>3.93(3H-s)<br>0.98(3H-t) | 5.18(1H-m)<br>1.70(2H-m) | 4.09(2H-d)<br>1.18(9H-s) | |

Table 3-continued

| Compound No. | (δ) ppm from TMs in CDCl₃ | | | |
|---|---|---|---|---|
| 36 | 7.0–7.7(4H-m)<br>3.92(3H-s)<br>1.16(6H-d) | 5.17(1H-m)<br>2.52(1H-m)<br>0.97(3H-t) | 4.07(2H-d)<br>1.69(2H-m) | |
| 37 | 6.5–7.2(4H-m)<br>2.26(3H-s) | 5.15(1H-m)<br>1.95(3H-s) | 3.87(2H-d)<br>1.28(3H-d) | |
| 38 | 7.0–7.7(4H-m)<br>3.93(3H-s) | 5.23(1H-m)<br>1.30(3H-d) | 4.05(2H-d)<br>1.20(9H-s) | |
| 39 | 7.0–7.7(4H-m)<br>3.92(3H-s)<br>1.15(6H-d) | 5.29(1H-m)<br>2.52(1H-m) | 4.04(2H-d)<br>1.30(3H-d) | |
| 40 | 7.10(1H-m)<br>3.94(2H-d)<br>1.16(9H-s) | 6.84(3H-m)<br>3.75(3H-s)<br>0.96(3H-t) | 5.09(1H-m)<br>1.74(2H-m) | |
| 41 | 7.04(1H-m)<br>3.97(2H-d)<br>1.75(2H-m) | 6.81(3H-m)<br>3.74(3H-s)<br>1.17(6H-d) | 5.13(1H-m)<br>2.51(1H-m)<br>0.96(3H-t) | |
| 42 | 7.10(1H-m)<br>3.99(2H-d)<br>1.18(9H-s) | 6.77(3H-m)<br>2.53(2H-q)<br>~1.2(3H-t) | 5.10(1H-m)<br>1.74(2H-m)<br>0.94(3H-t) | |
| 43 | 7.10(1H-m)<br>2.54(2H-q)<br>~1.2(3H-t) | 6.79(3H-m)<br>2.5(1H-m)<br>1.14(6H-d) | 5.13(1H-m)<br>1.76(2H-m)<br>0.94(3H-t) | 3.98(2H-d) |
| 44 | 6.97(4H-s)<br>3.89(3H-s)<br>0.97(3H-t) | 5.18(1H-m)<br>1.70(2H-m) | 4.08(2H-d)<br>1.18(9H-s) | |
| 45 | 6.96(4H-s)<br>3.89(3H-s)<br>1.18(6H-d) | 5.17(1H-m)<br>2.51(1H-m)<br>0.98(3H-t) | 4.08(2H-d)<br>1.70(2H-m) | |
| 46 | 6.8–7.2(4H-m)<br>2.63(2H-q)<br>~1.2(3H-t) | 5.19(1H-m)<br>1.67(2H-m)<br>0.97(3H-t) | 4.04(2H-d)<br>1.20(9H-s) | |
| 47 | 6.8–7.2(4H-m)<br>2.63(2H-q)<br>~2.5(1H-m) | 5.17(1H-m)<br>1.66(2H-m)<br>~1.2(3H-t) | 4.01(2H-d)<br>1.18(6H-d)<br>0.96(3H-t) | |
| 48 | 8.04(2H-d)<br>2.60(1H-s) | 6.94(2H-d)<br>1.53(2H-m) | 4.32(2H-q)<br>1.31(3H-t) | 3.95(3H-m)<br>1.00(3H-t) |
| 49 | 8.07(2H-d)<br>2.50(1H-s) | 7.00(2H-d)<br>1.40(3H-t) | 4.37(2H-q)<br>1.29(3H-d) | 4.00(3H-m) |
| 50 | 7.98(2H-d)<br>2.54(3H-s) | 6.97(2H-d)<br>1.66(2H-m) | 4.02(3H-m)<br>1.03(3H-t) | |
| 51 | 7.98(2H-d)<br>2.53(3H-s) | 6.98(2H-d)<br>1.31(3H-d) | ~4.2(4H-m) | |
| 52 | 7.28(2H-d)<br>2.71(1H-s) | 6.90(2H-d)<br>2.58(2H-q) | ~4.3(3H-m)<br>1.54(2H-m) | ~1.2(6H-m) |
| 53 | 7.16(2H-d)<br>3.2(1H-s) | 6.81(2H-d)<br>2.59(2H-q) | 3.85(3H-m)<br>~1.2(6H-m) | |
| 54 | 7.30(2H-d)<br>2.70(1H-s) | 6.84(2H-d)<br>1.65(2H-d) | 3.90(3H-m)<br>1.02(3H-t) | |
| 55 | 7.28(2H-d)<br>2.71(1H-s) | 6.83(2H-d)<br>1.29(3H-d) | ~3.9(3H-m) | |
| 56 | 6.90(4H-s)<br>3.30(1H-s) | 3.88(3H-m)<br>1.55(2H-d) | 3.71(3H-s)<br>0.99(3H-t) | |
| 57 | 7.96(2H-d)<br>4.0(3H-m) | 6.94(2H-d)<br>1.60(2H-m) | 4.9(1H-s)<br>1.02(3H-t) | |
| 58 | ~7.4(4H-m)<br>2.66(1H-s) | ~~4.0(3H-m)<br>1.64(2H-m) | 3.94(3H-s)<br>1.03(3H-t) | |
| 59 | ~7.0(4H-m)<br>2.25(3H-s) | 4.04(1H-m)<br>1.14(3H-d) | 3.7(3H-m) | |
| 60 | 6.95(4H-s)<br>3.6(1H-s) | 3.94(3H-m)<br>1.85(2H-m) | 3.80(3H-s)<br>1.00(3H-t) | |

The compounds of formula (I) can be obtained by addition-reaction of phenol or substituted phenols of the following formula (II)

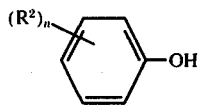

wherein $R^2$ and $n$ are the same as defined above, with epoxides of the following formula (III)

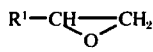

wherein $R^1$ is the same as defined above, in the presence of bases thereby to convert them to phenoxy- or substituted phenoxy-ethanol compounds of the general formula (IV)

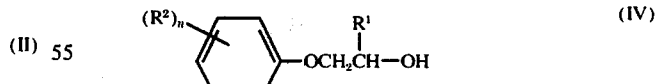

wherein $R^1$, $R^2$ and $n$ are the same as defined above.

Reaction of the resulting phenoxy- or substituted phenoxy-ethanol compounds of formula (IV) with carboxylic acids or derivatives thereof expressed by the following general formula (V)

$$R^3COX \qquad (V)$$

wherein $R^3$ is the same as defined above, and X is a substituent, such as a halogen atom or a hydroxyl or acyloxy group, capable of forming an ester bond upon splitting off, affords esters of phenoxy- or substituted phenoxy-ethanol expressed by the following formula (VI)

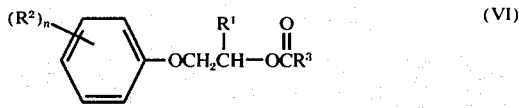

wherein $R^1$, $R^2$, $R^3$ and $n$ are the same as defined above.

Example of the phenol or substituted phenols of the formula (II) are phenol, o, m or p-hydroxybenzoic acid ester, o-, m- or p-chlorophenol, o-, m- or p-hydroxyacetophenone, o-, m- or p-alkylphenols, and o-, m- or p-alkoxyphenols.

The reaction of the phenol or substituted phenol of formula (II) with the epoxide compound of formula (III) can be performed in the presence of a base such as an alkali metal hydroxide, preferably sodium hydroxide or potassium hydroxide. Preferably, this reaction is carried out by adding a catalytic amount of the base to a substantially equimolar mixture of starting compounds, and heating the mixture in a closed vessel at a temperature of about 100° C. If desired, a solvent that does not interfere with the reaction can be used. The reaction is completed usually within several hours.

Isolation of the final product of formula (IV) from the reaction mixture is performed, for example, by extracting the reaction mixture with an extracting solvent such as ethyl acetate, washing the extract with water, drying it and distilling off the solvent to get the final intended product. In some case, the final product of high purity can be isolated only by distillation.

Examples of the carboxylic acids or derivatives thereof of formula (V) to be used to esterify the compounds of formula (IV) are alkylcarboxylic acids such as acetic acid, propionic acid, isobutyric acid, isovaleric acid, pivalic acid or lauric acid, and halides or anhydrides of these carboxylic acids.

The esterification reaction can be easily performed by stirring the reactants in an inert solvent such as benzene, chloroform or ether, preferably in the presence of a condensation promotor. Where an acid halide or acid anhydride is used as the carboxylic acid derivative of formula (V), the condensation promotor is preferably a basic substance, for example, an amine compound such as pyridine or triethyl amine. When the carboxylic acid of formula (V) is used, it is preferred to use p-toluenesulfonic acid, or sulfuric acid as the condensation promotor. When an acid halide is used as the carboxylic acid derivative of formula (V), a basic substance such as pyridine can be used as a medium having the activities both as a solvent and as a promotor.

In performing the present invention, the compounds of formula (IV) and (V) are conveniently used in substantially equimolar amounts. The reaction proceeds well at room temperature, but the reaction can be accelerated at a higher temperature, if desired.

The final product of formula (VI) can be isolated from the reaction mixture by extracting the reaction mixture with an extraction solvent such as ethyl acetate, washing the extract with water, drying it, and then distilling off the solvent. The purity of the product can be increased by column chromatography.

The compounds of this invention expressed by formula (IV) or (VI) exhibit strong juvenile hormone activities, and by treating insects in the egg stage or the larval stage with these compounds, they exhibit ovicidal activities, larvicidal activities and metamorphosisinhibiting activities, and prevent normal pupation and emergence. Even if the larvae normally metamorphose and grow into adults, their genital function is impeded, and coitus and ovideposition fail. Accordingly, these novel compounds of this invention have been found to be effective for pest control.

It has also been found that when silkworm larvae are treated with the compounds of this invention, their metamorphosis can be retarded and as a result, the yield of the cocoon increases.

When the compounds of this invention are used for pest control, it is advisable to use them in an effective concentration as a solution in a solvent such as acetone, benzene, toluene and xylene. Water may be added to this solution to form an emulsion. The effective concentration of the compounds of this invention in such a solution or emulsion can be optionally determined by those skilled in the art.

The compounds of this invention can be used together with other chemicals or fertilizers, etc.

When the compounds of this invention are applied for controlling pests on plants, the general practice is to spray the above solution or emulsion onto the plants. Alternatively, the plants can be immersed in the solution or emulsion. Preferably, these compounds are applied to the pests while they are in the egg or larval stage.

When the compounds of this invention are used for increasing the yield of cocoon, silkworms in the 4th to 6th larval instars, preferably before or after the 5th instar, are topically applied, sprayed or fed with these compounds. For topical application or spraying, the compounds are used as a solution or emulsion in a suitable solvent. In the case of feeding, the compounds are used as a combination of the solution or emulsion with a suitable carrier in the mixed or adsorbed state.

The compounds of this invention are non-toxic to human, have resistance to decomposition, exhibit superior effects, and are easy to apply, as compared with other juvenile hormones. Accordingly, the compounds of this invention are very effective for pest control and increased production of silkworm cocoons.

The present invention is illustrated by the following examples (Examples 1 to 19) of producing the compounds of this invention, and examples (Examples 20 to 25) of using such compounds.

EXAMPLE 1

A pressure glass vessel was charged with 16.7g (0.1 mol) of ethyl p-hydroxybenzoate, 6.4g (0.1 mol) of propylene oxide and 0.8 ml of a 50% aqueous solution of sodium hydroxide, and they were well stirred. Then the mixture was heated at 140° C for 4 hours.

The reaction mixture was extracted with ethyl acetate. The extract was washed with water, dried over anhydrous sodium sulfate, and concentrated to leave 20.4g of 1-(p-ethoxycarbonyl-phenoxy)-propan-2-ol (compound No. 49) in a yield of 86.9%. This compound was nearly pure, but when recrystallized from a mixture of n-hexane and benzene, a purer product having a melting point of 52° to 53° C was obtained. The infrared absorption spectrum of this product showed prominent peaks at 3420, 1705, 1605, 1270, 1170, 1119 (cm$^{-1}$).

EXAMPLE 2

In a closed vessel 16.7g of ethyl p-hydroxybenzoate, 7.2 g of 1,2-butylene oxide and 0.8 ml of a 50% aqueous solution of sodium hydroxide were heated at 150° C for 4 hours in the same manner as in Example 1. The reaction mixture obtained was treated in the same way as in Example 1 to afford 19.6g of 1-(p-ethoxycarbonylphenoxy)-butan-2-ol (compound No. 48) in an 82% yield, which had a melting point of 52° to 52.5° C when recrystallized from ethyl acetate and n-hexane.

EXAMPLE 3

The same reaction as in Example 1 was performed except that 11 g of mcresol was used instead of the ethyl p-hydroxybenzoate. The resulting reaction mixture was distilled directly to afford 13.0g of 1-(m-cresoxy)-propan-2-ol (compound No. 59) in a yield of 74.7.7%, which had a boiling point of 119°–122° C/5 mmHg.

EXAMPLE 4

In a closed vessel 12.2g (0.1 mol) of p-ethylphenol, 7.2 g (0.1 mol) of 1,2-butylene oxide and 0.8 ml of a 50% aqueous solution of sodium hydroxide were heated at 140° to 145° C for 4 hours in the same way as in Example 1. The reaction mixture obtained was treated in the same way as in Example 1 to afford 14.8 g of 1-(p-ethylphenoxy)-butan-2-ol (compound No. 52) in a yield of 76.3%.

EXAMPLE 5

The same reaction as in Example 4 was carried out except that 12.8g of p-chlorophenol was used instead of the p-ethylphenol. The resulting reaction mixture was purified by column chromatography using alumina to afford 16.9g of 1-(p-chlorophenoxy)-butan-2-ol (compound No. 54) as a colorless oily substance in an 84.5% yield.

EXAMPLE 6

The same reaction as in Example 1 was carried out except that 13.6g of p-hydroxyacetophenone was used instead of the ethyl p-hydroxybenzoate. The reaction mixture was purified by column chromatography using alumina to afford 17.8g of 1-(p-acetylphenoxy)-propan-2-ol (compound No. 51) as a colorless oily substance in an 89% yield.

EXAMPLE 7

In pyridine (10ml) 1.2 g (5 mmol) of 1-(p-ethoxycarbonyl-phenoxy)-butan-2-ol was dissolved and to this solution was gradually added 0.6 g (5 mmol) of pivaloyl chloride cooling in an ice bath. The mixture was stirred at room temperature for 3 hours after the addition was completed. During the course of the reaction pyridine hydrochloride precipitated. The reaction mixture was then poured in ice water and extracted with ethyl acetate. The extract was washed with water, dried, and concentrated to afford 1.6g of 1-(p-ethoxycarbonyl-phenoxy)-butan-2-ol pivalate (compound No. 1) in a yield of 89% as a light yellow viscous oily substance.

Thin layer chromatographic analysis of this product showed that it was nearly pure. When the product was purified by column chromatography using silica gel, a pure substance was obtained as colorless prisms having a melting point of 46° to 48° C.

Infrared absorption: 1720, 1605, 1280, 1255, 1165, 1105 (cm$^{-1}$).

EXAMPLE 8

The procedure of Example 7 was repeated except that 0.6 g of isovaleroyl chloride was used instead of the pivaloyl chloride. There was obtained 1.6g of 1-(p-ethoxycarbonyl-phenoxy)-butan-2-ol isovalerate (compound No. 2) in a yield of 90% as a colorless oily substance.

EXAMPLE 9

In pyridine (10 ml) 1.3 g of 1-(m-cresoxy)-propan-2-ol and 1.1g of acetic anhydride were dissolved and the solution was allowed to stand overnight with stirring at room temperature. The reaction mixture was poured in ice water, and extracted with ethyl acetate. The extract was washed with water, dried over anhydrous magnesium sulfate, and concentrated under reduced pressure. The residue was distilled to afford 1.4g of 1-(m-cresoxy)-propan-2-ol acetate (compound No. 37) in a yield of 86.5% as an oily substance having a boiling point of 96° to 98° c/ 0.7 mmHg.

EXAMPLE 10

Cooling in an ice bath 0.93 g (5 mmol) of 1-(p-ethylphenoxy)-butan-2-ol was dissolved in 10 ml of pyridine, and to this solution was added dropwise 0.53 g (5 mmol) of isobutyryl chloride. The mixture was stirred at room temperature for 3 hours after the addition was completed. The reaction mixture was treated in the same manner as in Example 7, and purified by column chromatography using silica gel to afford 1.3 g of 1-(p-ethylphenoxy)-butan-2-ol isobutyrate (compound No. 15) in a yield of 83% as a colorless oily substance. The refractive index of the product was $n_D^{32} = 1.4799$.

EXAMPLE 11

The procedure of Example 7 was repeated except that 1.0g of 1-(p-chlorophenoxy)-propan-2-ol was used instead of the 1-(p-ethoxycarbonyl-phenoxy)-butan-2-ol. The reaction mixture was purified by column chromatography using silica gel to afford 1.2 g of 1-(p-chlorophenoxy)-propan-2-ol pivalate (compound No. 22) as a colorless oily substance in a 96.5% yield. This product had an $n_D^{32}$ of 1.4857.

EXAMPLE 12

The procedure of Example 10 was repeated except that 1.0g of 1-(p-acetylphenoxy)-propan-2-ol was used instead of 1-(p-ethylphenoxy)-butan-2-ol. There was obtained 1.1g of 1-(pacetylphenoxy)-propan-2-ol isobutyrate (compound No. 12) in a yield of 81% as a colorless oily substance having an $n_D^{32}$ of 1.5022.

EXAMPLE 13

The procedure of Example 7 was repeated except that 0.53 g of isobutyryl chloride was used instead of the pivaloyl chloride. There was obtained 1.54 g of 1-(p-ethoxycarbonyl-phenoxy)-butan-2-ol isobutyrate (compound No. 3) in a yield of 89% as a colorless oily substance having an $n_D^{32}$ of 1.4869.

The infrared absorption spectrum of this product showed prominent peaks at 1720, 1605, 1260, 1150, 1104, 850 (cm$^{-1}$).

EXAMPLE 14

The procedure of Example 7 was repeated except that 1.1 g of 1-(p-ethoxycarbonyl-phenoxy)-propan-2-ol was used instead of the 1-(p-ethoxycarbonyl-phenoxy)-butan-2-ol. There was obtained 1.7g of 1-(p-ethoxycarbonyl-phenoxy-propan-2-ol pivalate (compound No. 4) in a yield of 92% as a colorless oily substance having an $n_D^{32}$ of 1.4797. Infrared absorption: 1720, 1605, 1280, 1253, 1160 (cm$^{-1}$).

EXAMPLE 15

Cooling in an ice bath 1.1g (5 mmol) of 1-(p-ethoxycarbonyl-phenoxy)-propan-2-ol was dissolved in 10 ml of pyridine, and 0.6 g of isovaleroyl chloride was added dropwise to this solution. The mixture was stirred at room temperature for an additional 3 hours. The reaction mixture was treated in the same way as in Example 7, and purified by column chromatography using silica gel to afford 1.6g of 1-(p-ethoxycarbonyl-phenoxy)-propan-2-ol isovalerate (compound No. 5) in a yield of 90% as a colorless oily substance having an $n_D^{32}$ of 1.4885. Infrared absorption: 1715, 1605, 1260, 1160, 1103, 848 (cm$^{-1}$).

EXAMPLE 16

The procedure of Example 10 was repeated except that 1.0g (5 mmol) of 1-(p-acetylphenoxy)-butan-2-ol was used instead of the 1-(p-ethylphenoxy)-butan-2-ol. There was obtained 1.1g of 1-(p-acetylphenoxy)-butan-2-ol. Isobutyrate (compound No. 9) in a yield of 80% as a colorless oily substance having an $n_D^{32}$ of 1.4901. Infrared absorption: 1730, 1678, 1603, 1250, 1160, 835 (cm$^{-1}$).

EXAMPLE 17

The procedure of Example 7 was repeated except that 1.0g of 1-(p-acetylphenoxy)-propan-2-ol was used instead of the 1-(p-ethoxycarbonyl-phenoxy)-butan-2-ol. There was obtained 1.2g of 1-(p-acetylphenoxy)-propan-2-ol pivalate (compound No. 10) in an 82.3% yield as a colorless oily substance having an $n_D^{32}$ of 1.4933. The infrared absorption spectrum of this product showed prominent peaks at 1728, 1679, 1603, 1255, 1160, 1110, 835 (cm$^{-1}$).

EXAMPLE 18

The procedure of Example 7 was repeated except that 0.93 g (5 mmol) of 1-(p-ethylphenoxy)-butan-2-ol was used instead of the 1-(p-ethoxycarbonyl-phenoxy)-butan-2-ol. There was obtained 1.0g of 1-(-ethylphenoxy)-butan-2-ol pivalate (compound No. 13) in a 92.3% yield as a colorless oily substance having an $n_D^{32}$ of 1.4750. Infrared absorption: 1720, 1605, 1280, 1241, 1150 (cm$^{-1}$).

EXAMPLE 19

The procedure of Example 7 was repeated except that 1.0g (5 mmol) of 1-(p-chlorophenoxy)-butan-2-ol was used instead of the 1-(p-ethoxycarbonyl-phenoxy)-butan-2-ol. There was obtained 1.2g of 1-(p-chlorophenoxy)-butan-rophenoxy) 2-ol pivalate (compound No. 19) in a yield of 92.3% as a colorless oily substance having an $n_D^{32}$ of 1.4908. The infrared absorption spectrum of this product showed prominent peaks at 1730, 1603, 1280, 1245, 1160 (cm$^{-1}$).

EXAMPLE 20

The solution of each of the test compounds shown in Table 4 in acetone was topically applied to the matured larvae of fall webworms (Hyphantria cunea) and then, their death, emergence, and coitus and ovideposition after emergence were observed. The results are shown in Table 4. In the control group, only acetone was applied topically.

Table 4

| Compound No. | Amount ($\gamma$) applied to each worm | Death rate (%) | Coitus rate (%) | Ovideposition rate (%) |
|---|---|---|---|---|
| 1 | 6.3 | 100 | 0 | 0 |
| 2 | 6.6 | 85 | 0 | 0 |
| 3 | 6.4 | 95 | 0 | 0 |
| 4 | 6.7 | 98 | 0 | 0 |
| 5 | 6.0 | 60 | 0 | 0 |
| 10 | 25.3 | 40 | 60 | 100 |
| Control | 0.8 μl | 0 | 100 | 100 |

EXAMPLE 21

The same test as in Example 20 was conducted using the matured larvae of Indian meal moths (*plodia interpunctella*), and the rate of pupation and the rate of abnormal pupation were examined. The results are shown in Table 5.

Table 5

| Compound No. | Amount of chemical ($\gamma$ for each moth) | Rate of pupation (%) | Rate of abnormal pupation (%) | Death rate (%) |
|---|---|---|---|---|
| m 1 | 0.625 | 80 | 88 | 20 |
| 4 | 0.625 | 50 | 85 | 40 |
| Control group | 0.8 μl | 100 | 0 | 0 |

In the control group, only acetone was used.

EXAMPLE 22

Eggs of blue willow leaf beetles (*Plagiodera uericolora*) were immersed in a solution of each of the compounds in acetone for 15 seconds to examine their ovicidal effects. The results obtained are shown in Table 6. In the control group, only acetone was used.

Table 6

| Compound No. | Concentration of solution (ppm) | Ovicidal rate (%) | Hatchability (%) |
|---|---|---|---|
| 1 | 100 | 100 | 0 |
| 4 | 100 | 85 | 15 |
| Control group | | 0 | 100 |

EXAMPLE 23

A solution of each of the test compounds shown in Table 7 was topically applied to the fifth instar silkworm larvae by 100 μg per caput. The average weight of the coocon cocoon was measured, and the results are shown in Table 7. In the control group, only acetone was applied topically.

Table 7

| Compound No. | Weight of cocoon layer (mg) (average of 30 silkworms) |
| --- | --- |
| 1 | 585 |
| 2 | 560 |
| 3 | 525 |
| 9 | 516 |
| 13 | 572 |
| 19 | 486 |
| Control group | 400 |

EXAMPLE 24

A solution of compound No. 1 in acetone was sprayed on the fifth instar silkworm larvae, and the effective amount of the compound was measured. The results are shown in Table 8. In the control group, only acetone was used.

Table 8

| Amount of chemical (γ for each silkworm) | Cocooning rate (%) | Average weight of the cocoon layer (average of 30 silkworms) (mg) |
| --- | --- | --- |
| 1000 | 20 | 150 |
| 500 | 40 | 320 |
| 100 | 100 | 580 |
| 50 | 100 | 530 |
| 25 | 100 | 480 |
| 12.5 | 100 | 450 |
| Control group | 100 | 405 |

EXAMPLE 25

A solution of each of the test compounds as indicated in Table 9 in acetone was injected into the fifth instar silkworm larvae by 10 λg per capita, and the increase in the yield of cocoons was examined. In the control group, only acetone was injected. The results are shown in Table 9.

Table 9

| Compound No. | Weight of the cocoon layer (average of 30 silkworms) |
| --- | --- |
| 1 | 525 |
| 2 | 518 |
| 3 | 502 |
| 9 | 485 |
| 13 | 518 |
| 19 | 460 |
| Control group | 420 |

What we claim is;

1. A substituted β-phenoxy-ethanol ester expressed by the following formula:

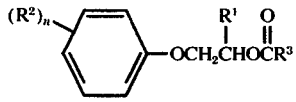

wherein $R^1$ is a hydrogen atom, straight-chain or branched-chain alkyl group having 1 – 6 carbon atoms, $R^2$ is a carboalkoxy group containing 1 to 6 carbon atoms in the alkyl moiety, $R^3$ is an alkyl group containing 1 to 12 carbon atom and $n$ in a number from 1 to 3.

2. The compound of claim 1 which is 1-(p-ethoxycarbonyl-phenoxy)-butan-2-ol pivalate.

3. The compound of claim 1 which is 1-(p-ethoxycarbonyl-phenoxy)-butan-2-ol isovalerate.

4. The compound of claim 1 which is 1-(p-ethoxycarbonyl-phenoxy)-butan-2-ol isobutyrate.

5. The compound of claim 1 which is 1-(p-ethoxycarbonyl-phenoxy)-propan-2-ol pivalate.

6. The compound of claim 1 which is 1-(p-ethoxycarbonyl-phenoxy)-propan--(p-ethoxycarbonyl-phenoxy)-propan--ol isovalerate.

7. The compound of claim 1 which is 1-(p-isopropoxycarbonyl-propan-2-ol pivalate.

8. The compound of claim 1 which is 1-(p-isopropoxycarbonyl-phenoxy)-butan-2-ol pivalate.

* * * * *

UNITED STATES PATENT OFFICE
CERTIFICATE OF CORRECTION

Patent No. 4,016,186          Dated April 5, 1977

Inventor(s) KIYOSHI KONDO, et al.

It is certified that error appears in the above-identified patent and that said Letters Patent are hereby corrected as shown below:

On the Cover Page add:

[30] FOREIGN APPLICATION PRIORITY DATA

Nov. 27, 1973    Japan    132148/73

Nov. 27, 1973    Japan    132149/73

Col. 3, Table 3, Third Column 11th entry from the bottom:

"5.18 (1H-m)" should be --5.19 (1H-m)--

Col. 9, line 19, "74.7.7%" should be --74.7%--.

Col. 11, line 64, delete "rophenoxy)".

Col. 13, line 39, "$\lambda$" should be --$\mu$--.

Col. 14, line 27, "atom" should be --atoms--.

UNITED STATES PATENT OFFICE
CERTIFICATE OF CORRECTION

Patent No. 4,016,186    Dated April 5, 1977

Inventor(s) Kiyoshi Kondo, et al.

It is certified that error appears in the above-identified patent and that said Letters Patent are hereby corrected as shown below:

Column 14, lines 36 and 37, "(p-ethoxycarbonyl-phenoxy)-propan--ol isovalerate." should read -- 2-ol-isovalerate --.

Column 14, claim 7 should read:

--7. The compound of claim 1 which is 1-(p-isopropoxy-carbonyl-phenoxy)-propan-2-ol pivalate. --.

Signed and Sealed this

Fourteenth Day of June 1977

[SEAL]

Attest:

RUTH C. MASON
Attesting Officer

C. MARSHALL DANN
Commissioner of Patents and Trademarks